United States Patent
Lee et al.

(10) Patent No.: US 7,431,466 B2
(45) Date of Patent: Oct. 7, 2008

(54) SOLAR SIMULATOR USING A COMBINATION OF MERCURY AND HALOGEN LAMPS

(75) Inventors: Jae-Myung Lee, Chungcheongnam-Do (KR); Gun-Young Park, Incheon (KR); Sang-Hwa Baek, Chungcheongnam-Do (KR); Jeong-Yong Lee, Gyeonggi-Do (KR); Gil-Sang Nam, Chungcheongnam-Do (KR); Sang-Hoon Kim, Chungcheongnam-Do (KR); Baek-Hee Jeong, Chungcheongnam-Do (KR)

(73) Assignee: Agency for Defense Development, Daejeon (KR)

( * ) Notice: Subject to any disclaimer, the term of this patent is extended or adjusted under 35 U.S.C. 154(b) by 304 days.

(21) Appl. No.: 11/177,852

(22) Filed: Jul. 8, 2005

(65) Prior Publication Data
US 2006/0176694 A1    Aug. 10, 2006

(30) Foreign Application Priority Data
Feb. 4, 2005   (KR)   ...................... 10-2005-0010787

(51) Int. Cl.
*F21V 9/02*   (2006.01)
(52) U.S. Cl. ................. 362/2; 362/1; 362/17; 362/230; 362/231

(58) Field of Classification Search ....................... None
See application file for complete search history.

(56) References Cited

U.S. PATENT DOCUMENTS

| | | | | |
|---|---|---|---|---|
| 3,202,811 A | * | 8/1965 | Hall, Jr. ........................ 362/2 |
| 3,870,873 A | * | 3/1975 | Mallory ......................... 362/2 |
| 4,163,342 A | * | 8/1979 | Fogg et al. ............... 47/58.1 R |
| 4,918,953 A | * | 4/1990 | Newman ...................... 70/131 |
| 5,259,812 A | * | 11/1993 | Kleinsek ...................... 454/57 |
| 5,315,834 A | * | 5/1994 | Garunts et al. ................ 62/78 |
| 5,623,149 A | * | 4/1997 | Kilmer ..................... 250/495.1 |
| 6,590,149 B2 | * | 7/2003 | Adelhelm ................... 136/246 |

* cited by examiner

*Primary Examiner*—Sandra O'Shea
*Assistant Examiner*—Danielle Dunn
(74) *Attorney, Agent, or Firm*—Brooks Kushamn P.C.

(57) ABSTRACT

A solar simulator combines mercury lamps and halogen lamps, to improve upon conventional solar simulators using halogen and infrared lamps which cannot recreate an environment close to that under real sunlight, and upon solar simulators using expensive and fragile metal halide lamps and arc xenon lamps. An environment recreation laboratory for solar simulation includes a lamp bank mounted at an upper portion thereof and including a plurality of halogen lamps, halogen filter lamps being halogen lamps provided with an infrared filter, respectively, and mercury lamps. A temperature control unit includes a cooling unit that discharges air to cool the lamp bank, and an air conditioner that distributes the air discharged by the cooling unit. An electrical panel controls operations of the lamp bank and the temperature control unit, such that an environment within the environment recreation laboratory may very closely simulate the environment under real sunlight.

15 Claims, 5 Drawing Sheets

SOLAR SIMULATOR USING A COMBINATION OF MERCURY AND HALOGEN LAMPS

BACKGROUND OF THE INVENTION

1. Field of the Invention

The present invention relates to a solar simulator, and particularly, to a solar simulator using a combination of mercury and halogen lamps so as to be capable of providing an environment with an illumination and a temperature approximating daily changes of radiated sunlight by combining commercial mercury lamps, halogen lamps and halogen filter lamps having an infrared filter.

2. Description of the Background Art

In general, an environment recreation laboratory (testing room) is installed indoors. In the environment recreation laboratory, performance and durability of a subject to be tested (sample) is examined within an environment approximating the natural environmental conditions. In order to successfully carry out the performance and durability test on various goods and weapons, equipment for an environment recreation test, which is arranged within the environment recreation laboratory, should be able to recreate conditions approximating the natural environment as much as possible.

A solar simulator, a lighting device arranged in the environment recreation laboratory, uses a halogen lamp or an infrared lamp to simulate sunlight. However, the halogen lamp and the infrared lamp cannot create all the wavelengths of sunlight. Therefore, to improve the accuracy of the environment recreation test, it is better to perform the test under conditions of actual sunlight than in the environment recreation laboratory.

Also, some solar simulators simulate the spectral wavelengths of sunlight by using a metal-halide lamp or an arc xenon lamp, but are problematic for several reasons: expensive lamps and difficult manipulation.

SUMMARY OF THE INVENTION

Therefore, it is an object of the present invention to provide a solar simulator using a combination of mercury and halogen lamps, which has a lamp bank in which commercial lamps are properly arranged to emit light, closely simulating sunlight, and which can approximate a daily change of sunlight radiated during a day by controlling a temperature and an irradiance within an environment recreation laboratory provided with the lamp bank.

Another object of the present invention is to provide a lamp bank that can simulate sunlight to provide the moderns who spend the most time indoors, with an environment similar to that under the real sunlight.

To achieve these and other advantages and in accordance with the purpose of the present invention, as embodied and broadly described herein, there is provided a solar simulator using a combination of mercury lamps and halogen lamps in an environment recreation laboratory for solar simulation, the solar simulator comprising: a lamp bank mounted at an upper portion of an environment recreation laboratory and including a plurality of halogen lamps, a plurality of mercury lamps and a plurality of halogen filter lamps being halogen lamps provided with infrared filters, respectively; a temperature control unit including a cooling unit that discharges air for removing high temperature heat generated by the lamp bank, and an air conditioner that distributes the air discharged by the cooling unit to the lamp bank; and an electrical panel for controlling operations of the lamp bank and the temperature control unit.

To achieve these and other advantages and in accordance with the purpose of the present invention, as embodied and broadly described herein, there is provided a lamp bank including a plurality of halogen lamps, a plurality of mercury lamps and a plurality of halogen filter lamps being halogen lamps provided with infrared filters, respectively, wherein the plurality of halogen filter lamps are arranged at a central portion thereof, the plurality of halogen lamps are arranged outwardly of the plurality of halogen filter lamps, and the plurality of mercury lamps are arranged outwardly of the plurality of halogen lamps.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a unit of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
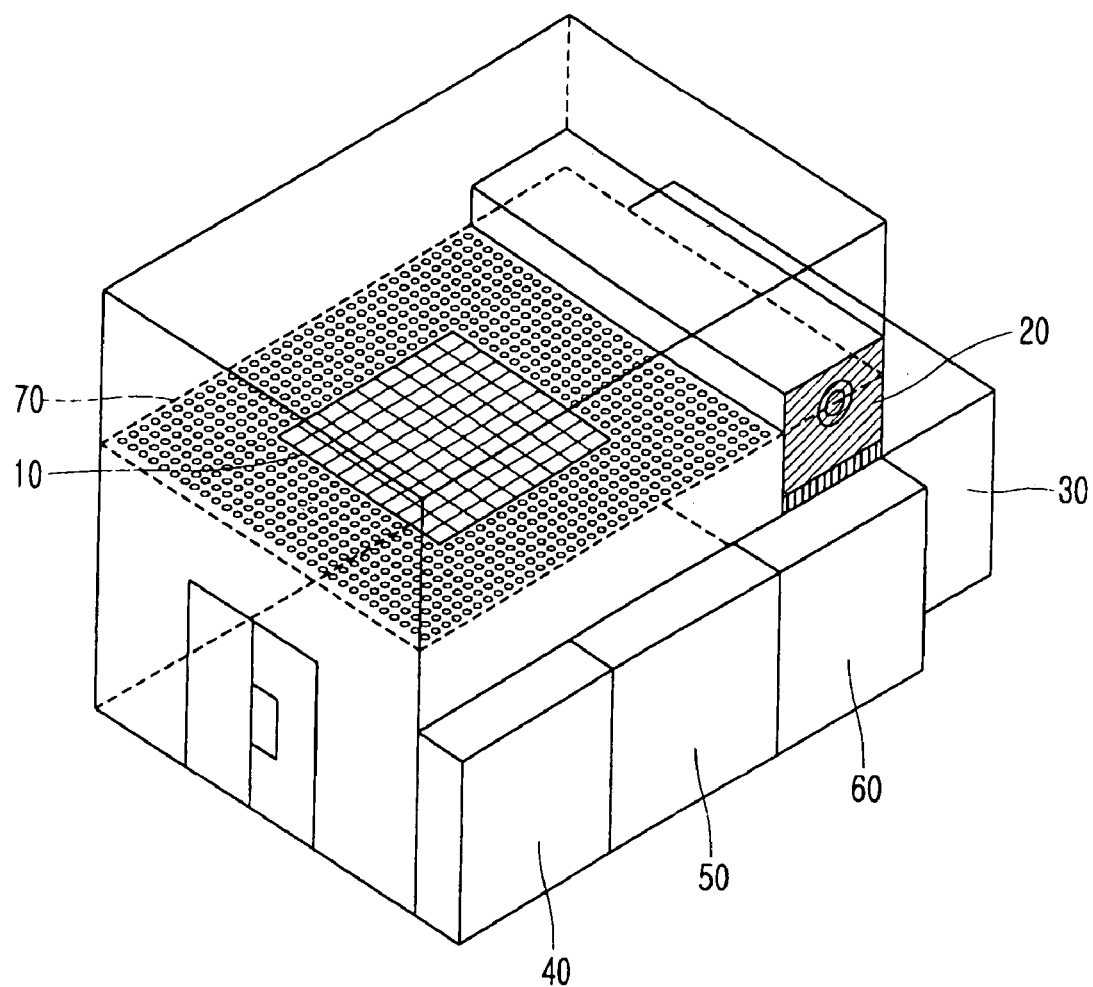
FIG. 1 illustrates a perspective view of an environment recreation laboratory implementing a solar simulator in accordance with the present invention.

FIG. 1 illustrates a perspective view of an environment recreation laboratory to which the solar simulator in accordance with the present invention is applied. As shown, the environment recreation laboratory includes a lamp bank 10 installed at an upper portion of the environment recreation laboratory and emitting light with three wavelengths, simulating sunlight, a cooling unit 30 for outputting cool air for removing high temperature heat generated by the lamp bank 10, an air conditioner 20 for dispensing the cool air outputted from the cooling unit 30, first, second and third electrical panels 40, 50 and 60 for controlling the lamp bank 10, the air conditioner 20 and the cooling unit 30, and a perforated plate 70 arranged on the same plane with the lamp bank.

A plurality of halogen lamps, halogen filter lamps and mercury lamps are arranged in a specific order so that the lamp bank 10 may create spectrums of infrared light, visible light and ultraviolet light, simulating sunlight.

The air conditioner 20 and the cooling unit 30 control the temperature within the environment recreation laboratory to create a desired environment, and remove the high temperature heat generated by the lamp bank 10 to extend a life span of each lamp.

To control an irradiance within the environment recreation laboratory, the first, second and third electrical panels 40, 50 and 60 control ON/OFF operation of each lamp constituting the lamp bank 10. Also, to control the temperature, those panels control the air conditioner 20 and the cooling unit 30.

The perforated plate 70 is installed on the same horizontal plane as the lamp bank 10, and has small holes so as to prevent the cool air from the air conditioner, which is discharged from a position that is higher than that of the lamp bank 10, from falling to the floor before flowing to the lamp bank 10.

Figure 2:
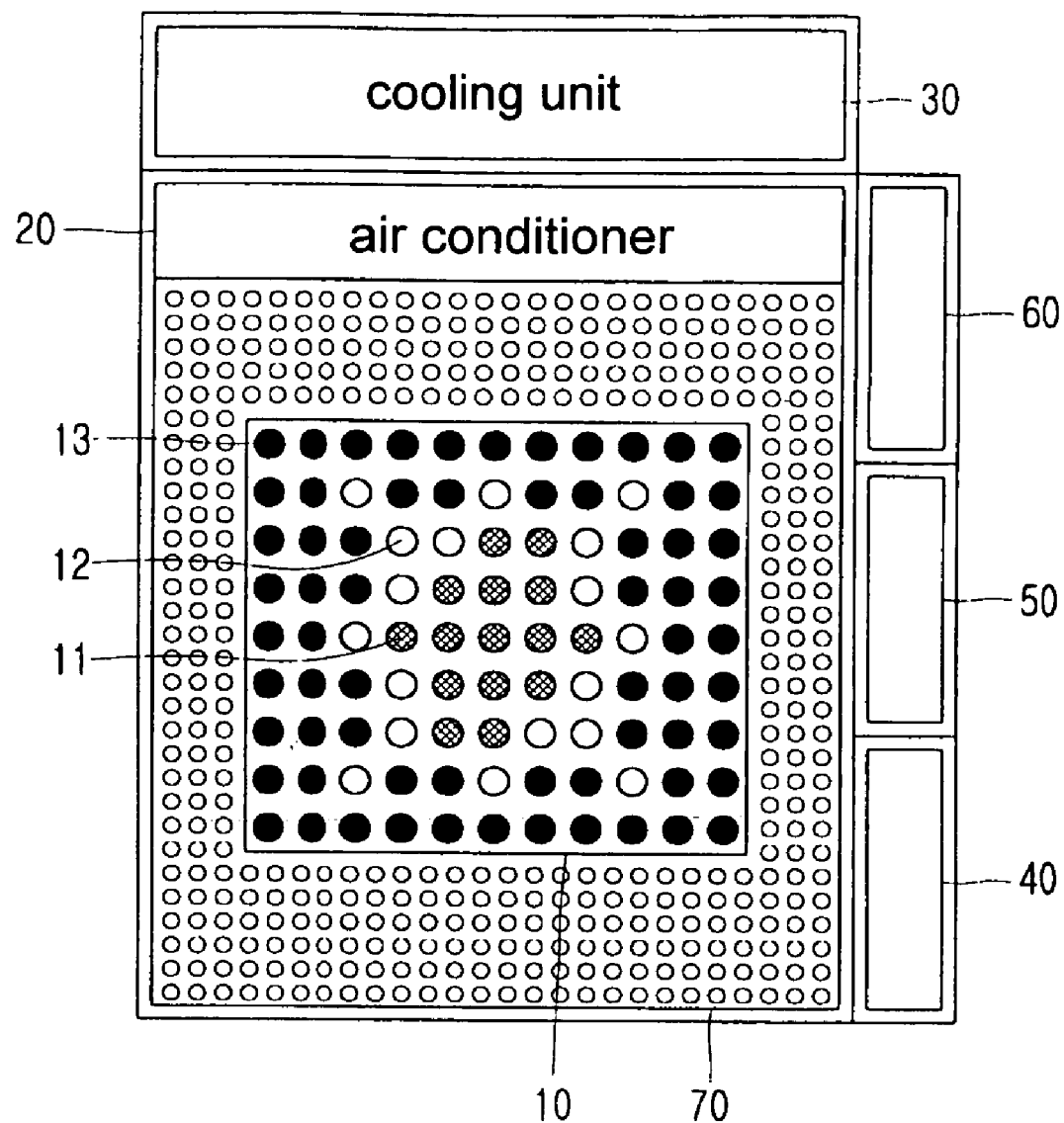
FIG. 2 is a top plan view which illustrates a lamp bank comprising the solar simulator of the environment recreation laboratory in accordance with the present invention.

FIG. 2 illustrates an arrangement of a lamp bank in the environment recreation laboratory implementing the solar simulator in accordance with the present invention. Referring to FIG. 2, the lamp bank 10 includes commercially available halogen filter, halogen and mercury lamps 11, 12 and 13.

Here, the lamp bank 10 is constructed by a combination of those lamps 11, 12 and 13 in order to obtain irradiance values of infrared light, visible light and ultraviolet light regions, closely approximating sunlight.

In the case of the spectrum of light emitted by a halogen lamp, an irradiance value increases from a shorter wavelength to a longer wavelength. In contrast, the spectrum of actual sunlight has an irradiance decreased from a shorter wavelength to a longer wavelength. Therefore, if only halogen lamps 12 are used, the irradiance value is low at the ultraviolet light region and is large at the infrared light region, as compared to sunlight.

Therefore, mercury lamps 13 are arranged to compensate a deficient irradiance at the ultraviolet light region. Also, halogen filter lamps 11 are used to decrease an irradiance at the infrared light region. Here, the halogen filter lamp 11 is a halogen lamp 12 provided with an infrared filter, thereby decreasing the amount of ultraviolet light emitted from the halogen lamp 12.

The lamp bank 10 should satisfy a condition of maintaining uniformity of the irradiance within the target area as well as a condition of having an irradiance per wavelength approximating that of sunlight. To this end, the halogen lamps 10 and the halogen filter lamps 11, the locations of which influence the uniformity of irradiance within the target area, are arranged at a central portion of the lamp bank 10, and the mercury lamps 13 whose locations have no influence on the uniformity of irradiance are arranged at an outer edge. In order that the lamp bank 10 emits an amount of infrared light approximating natural sunlight, the halogen filter lamps 11 are arranged inwardly of the halogen lamps.

Specifically, to determine the shape of the lamp bank 10, the x-axis coordinate and the y-axis coordinate of each lamp constituting the lamp bank 10 is calculated upon inputting to an existing simulation program, data about the distance ($H_0$) between a target or a sample (i.e., a subject to be tested) and the center of a center lamp, the intervals between lamps in both the line and column directions, longitudinal and horizontal lengths of the lamp bank, the number of lamps in both the line and column directions and a zenithal angle. In the present invention, the lamp bank 10 is set to be arranged on a plane parallel to the sample by setting the zenithal angle of the input data as 0°. The reason why the lamp bank 10 is set to be arranged on a plane parallel to the sample is that if the lamp bank 10 is not parallel thereto and has a zenithal angle which is not 0°, the columns are gathered at the center of the zenithal angle. Accordingly, the z coordinate of the lamp bank 10 becomes $H_0$, and the x-axis and y-axis coordinates are obtained as the simulation program calculates input data about the intervals between lamps in both the line and column directions, longitudinal and horizontal lengths of the lamp bank and the number of lamps in both the line and column directions.

According to one embodiment of the present invention, the halogen filter lamps 11, the halogen lamps 12 and the mercury lamps 13 constituting the lamp bank 10 may be disposed as illustrated in FIG. 2, respectively. The irradiance in each wavelength range (spectrum), obtained by experiment, is shown in the following Table 1.

TABLE 1

| Wavelength range (μm) | Irradiance (W/m$^2$) |
|---|---|
| 0.28-0.40 | 52.9 |
| 0.40-0.78 | 466 |
| 0.78-3.00 | 587 |

Namely, as shown in Table 1, the total irradiance was measured at 1106 W/m$^2$ within a range of ±10% of 1120 W/m$^2$. Also, from the experiment, it can be known that the illumination within a defined area (60 cm×60 cm) is uniform within the range of ±10% of 1120 W/m$^2$.

The perforated plate 70 is provided on the same plane as the lamp bank 10, and the size of the holes in the perforated plate 70 is smaller than the interval between the lamps constituting the lamp bank 10. The perforated plate 70 is formed so as to enable a large amount of the air discharged from the air conditioner 20 to reach the lamp bank 10. Namely, the perforated plate 70 having the small holes is arranged in order to prevent the denser cool air, which is discharged to a ceiling portion of the environment recreation laboratory from the air conditioner 20, from descending before reaching the lamp bank 10. Therefore, a large amount of cooling air can pass through the lamp bank 10.

Figure 3:
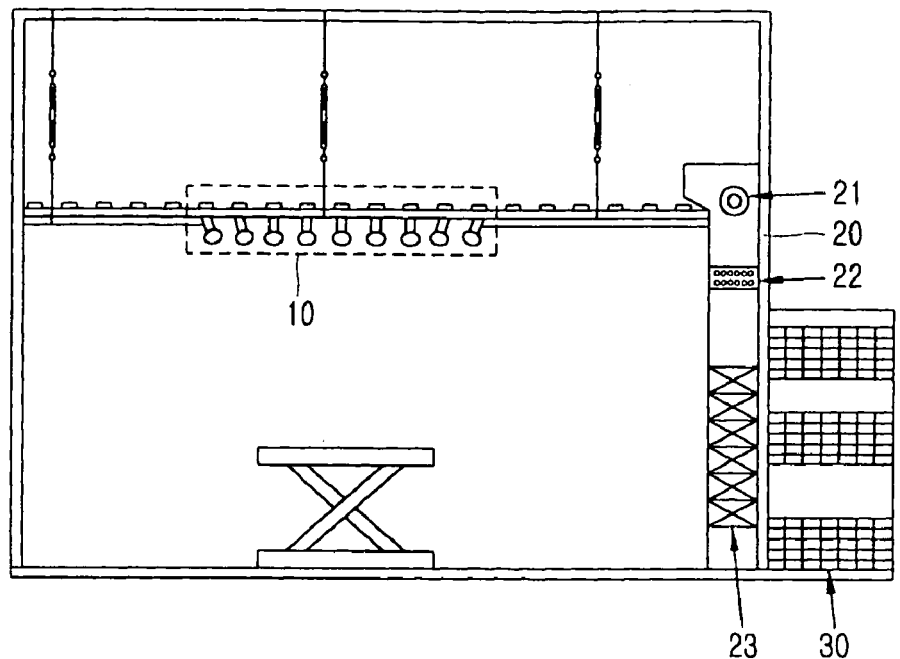
FIG. 3 is a side elevation view which illustrates an interior of the environment recreation laboratory implementing the solar simulator in accordance with the present invention.

FIG. 3 illustrates an interior of the environment recreation laboratory equipped with the solar simulator in accordance with the present invention. As illustrated, a sample is placed at the center of an area onto which light is emitted from the lamp bank 10 of the environment recreation laboratory. Also, the lamps arranged towards the outer edges are inclined inwardly at predetermined angles toward the center, i.e., towards the sample.

In the environment recreation laboratory, the air conditioner 20 and the cooling unit 30 for dispersing high temperature heat are arranged, thereby preventing a life span reduction of the lamps due to an increase in the temperature of the lamp bank 10. The cooling unit 30 includes a compressor, a condenser and a capillary tube, and a fluid refrigerant condensed in the cooling unit 30 is gasified in an evaporator 23 within the air conditioner 20 and discharged through a blower 21. A heater 22 within the air conditioner 20 controls a temperature of a gaseous refrigerant evaporated by the evaporator 23.

Figure 4A:
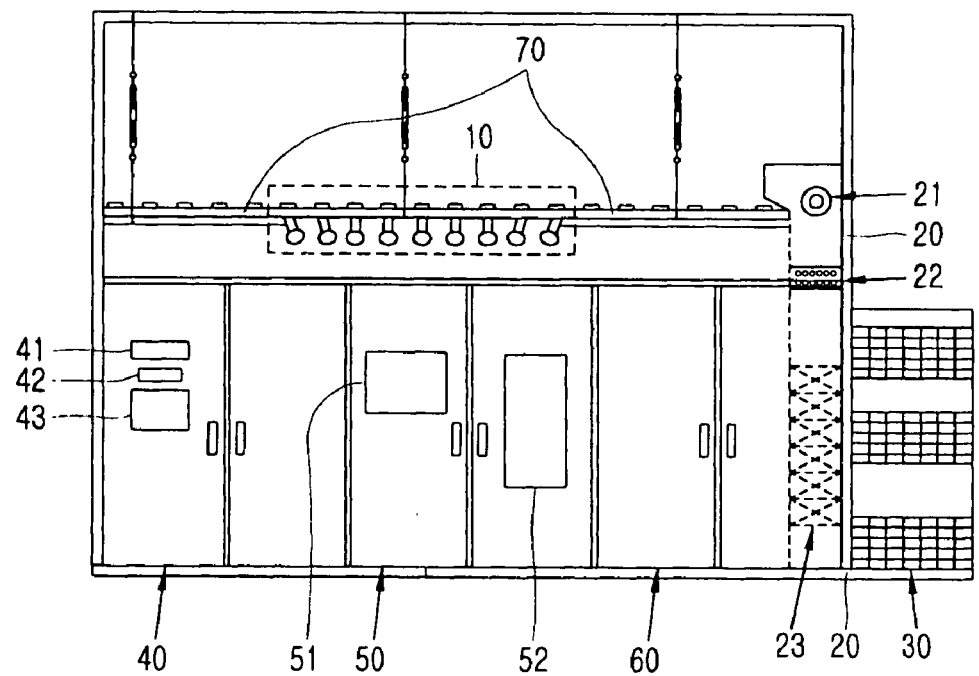
FIG. 4A illustrates a further side elevation view of the interior of the environment recreation laboratory implementing the solar simulator in accordance with the present invention.

FIG. 4A schematically illustrates a side view of the environment recreation laboratory equipped with the solar simulator in accordance with the present invention. As illustrated, first, second and third electrical panels 40, 50 and 60 for respectively controlling the lamp bank 10, the air conditioner 20 and the cooling unit 30 are provided at a side portion of the environment recreation laboratory.

Figure 4B:
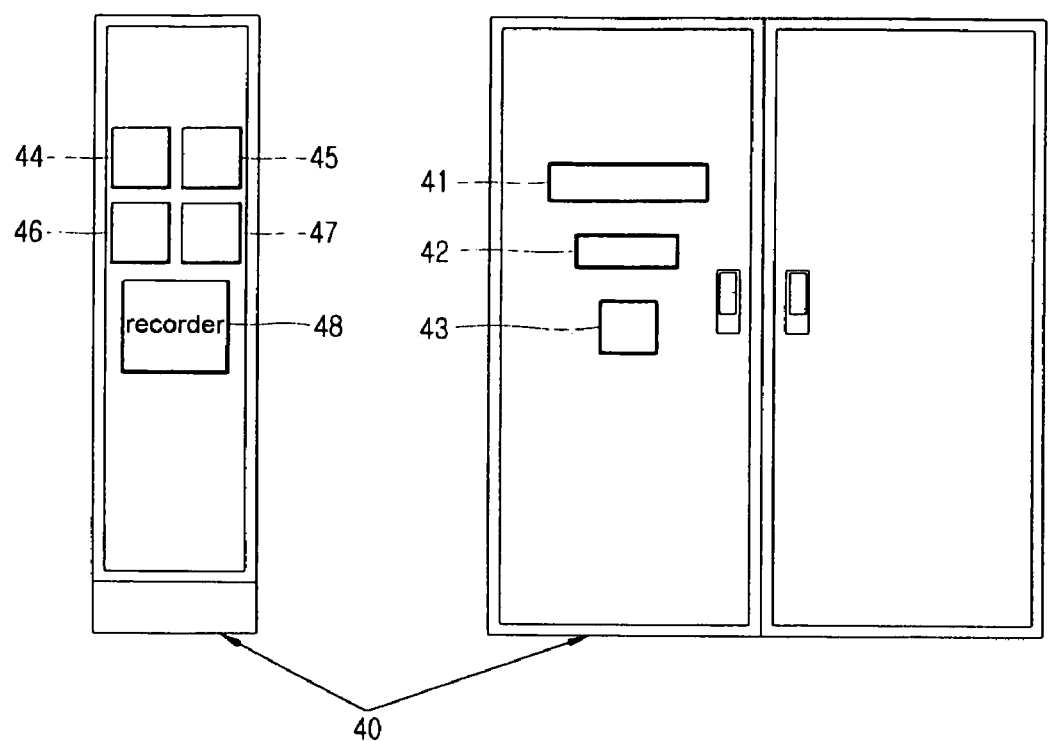
FIG. 4B schematically illustrates a first electrical panel of the solar simulator in accordance with the present invention.

FIG. 4B schematically illustrates a frontal elevation view and a left side elevation view. As illustrated, the first electrical panel 40 includes a blower/cooling unit operation indicator lamp 41 for indicating whether the blower 21 and cooling unit 30 are in operation based upon the lamp's lighting state, a blower/cooling unit operating switch 42 for operating the blower 21 and the cooling unit 30, a controller 43 storing reference values for controlling the blower 21 and the cooling unit 30 and reference values for controlling ON/OFF operation of the lamp bank 10, the controller 43 being responsible for a temperature and irradiance control in accordance with internal signals and a time signal, an irradiance display unit 44, a temperature display unit 45, a humidity display unit 46 and a wind velocity display unit 47 for measuring and displaying the irradiance, the temperature, the humidity and the wind velocity of the recreated environment, and a recorder 48 for recording changes in the irradiance, temperature, humidity and wind velocity in the environment recreation laboratory.

The controller 43 stores irradiance reference values and temperature reference values from sunrise to sunset to control the temperature and the irradiance, and controls the irradiance and the temperature within the environment recreation laboratory on the basis of the stored irradiance and temperature values.

As one embodiment, a controller made by OYO (model: U-6622P-CH3) may be used, and as the recorder 48, a commercially available model μR1800 made by YOKOGAWA may be used.

The second electrical panel 50 includes a lamp lighting checking unit 51 and a lamp switch 52. The second electrical panel 50 controls ON/OFF operation of each lamp of the lamp bank 10 and simultaneously checks a lighting state of each lamp.

As an example, a control process in accordance with the present invention to recreate the environment of a region undergoing an air temperature change from 30° C. to 44° C. and an irradiance change from 0 W/m² to 1120 W/m² during a day will now be described.

First, an irradiance variation and a temperature variation of the region to be recreated are inputted to the controller 43 and then power is inputted. Then, power is distributed to the lamp bank 10, the air conditioner 20, the cooling unit 30 and the first, second and third electrical panels 40~60, and the controller 43 of the first electrical panel 40 controls the irradiance within the environment recreation laboratory in accordance with the time signal.

Here, the time signal is divided into four levels. The time signal effectively controls the lamp bank, by virtue of the fact that as the level of the time signal increases, more lamps are turned on. Lamps turned on when the time signal corresponds to an upper level (e.g., third level) include those lamps turned on when the time signal corresponds to a lower level (e.g., second level). Also, the time signal at each level turns on at least one halogen filter lamp, one halogen lamp and one mercury lamp.

In one embodiment, it is set that a first level time signal is applied to the controller for one and one-half hours after sunrise, a second level time signal is applied for the next one and one-half hours, a third level time signal is applied for the next two hours, and a fourth level time signal is applied from 11:00 to 15:00 during which interval the irradiance and temperature are the highest. As the simulated daytime gets closer to sunset, the level of the time signal decreases. In order to realize an environment more closely simulating irradiance variation of the corresponding region, the time signal may have more minutely divided levels over time.

Also, the controller 43 controls the air conditioner 20 and the cooling unit 30 such that the room temperature measured by a temperature sensor (not shown) arranged within the environment recreation laboratory approaches the reference temperature value.

The third electrical panel 60 has therein a mercury lamp stabilizer (not IS shown) for maintaining a constant voltage of each mercury lamp 13, thereby maintaining a constant irradiance.

Figure 5A:
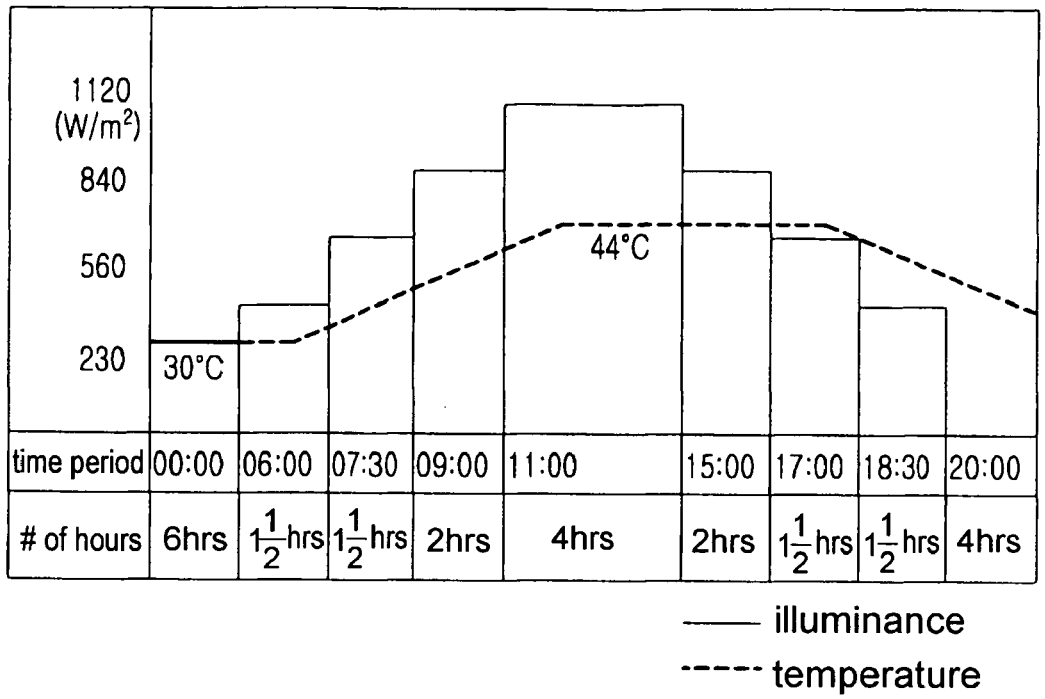
FIGS. 5A and 5B are graphs respectively showing irradiance profiles for actual sunlight and for light produced by the solar simulator in accordance with the present invention.
Figure 5B:
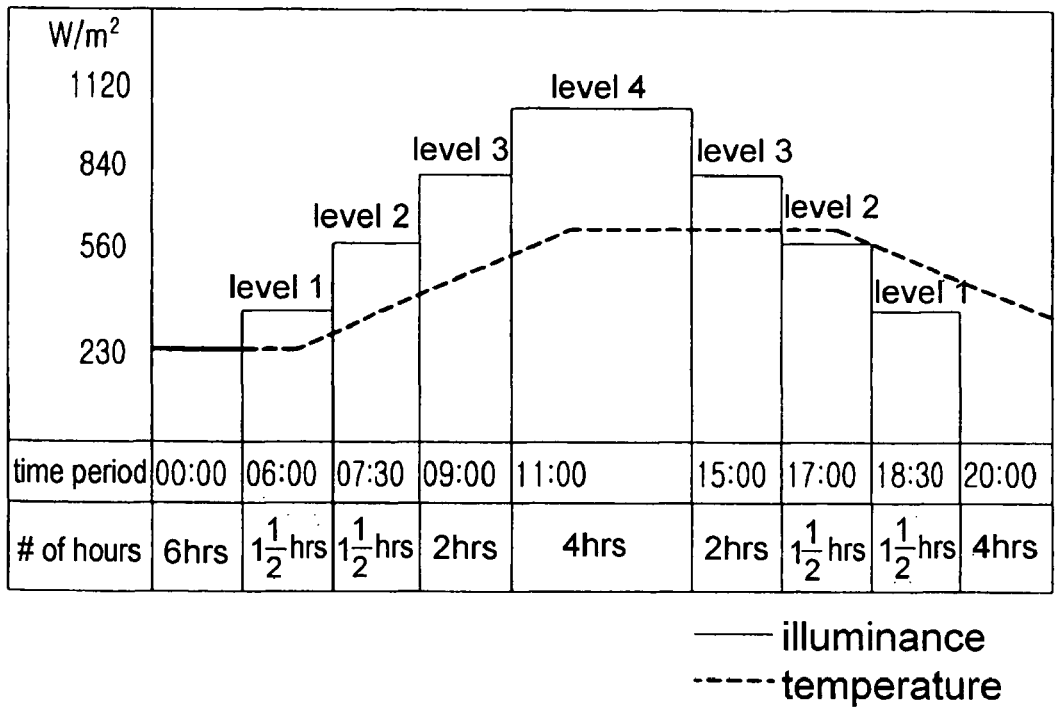

FIGS. 5A and 5B illustrate graphs showing irradiance profiles for actual sunlight and for light produced by the solar simulator in accordance with the present invention. FIG. 5A is a graph showing the irradiance profile for actual sunlight of an area, which is to be recreated by the present invention, to show changes in temperature and irradiance during the day. Referring to the graph, the air temperature is changed from 30° C. to 44° C. during the day, and the irradiance is changed from 0 W/m² to 1120 W/m². FIG. 5B is a graph showing temperature and irradiance changes within the environment recreation laboratory equipped with the solar simulator in accordance with the present invention. As the controller 43 controls the lamp bank 10, the air conditioner 20 and the cooling unit 30, a profile that is very similar to the graph of FIG. 5A can be obtained.

As so far described, by the present invention, an environmental condition within the environment recreation laboratory very closely simulates the environment produced by natural sunlight. The effects of the present invention will now be described.

First, without being affected by geographical and seasonal factors, a test using simulated solar energy can be performed under the conditions of a temperature of 49° C. and an irradiance of 1120 Wm2, which are typical of harsh environmental conditions required for testing by the military. Secondly, an environment close to the natural environment can be realized even by using relatively inexpensive commercially available lamps. Thirdly, as the lamps are optimally arranged for the test, the radiation uniformity within a target area is maintained within ±10%, and the time and cost required for the test can be reduced by ⅓. Lastly, the lamp bank used for the solar simulator may also be utilized in other applications, for example, the moderns who spend little time outdoors can be provided with simulated natural light even when indoors.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A solar simulator using a combination of mercury lamps and halogen lamps in an environment recreation laboratory for solar simulation, the solar simulator comprising:
   a lamp bank mounted at an upper portion of an environment recreation laboratory and including a plurality of halogen lamps, a plurality of mercury lamps and a plurality of halogen filter lamps being halogen lamps provided with infrared filters, respectively;
   a temperature control unit including a cooling unit that discharges air for removing high temperature heat generated by the lamp bank, and an air conditioner that distributes the air discharged by the cooling unit to the lamp bank; and an electrical panel for controlling operations of the lamp bank and the temperature control unit;

wherein in the lamp bank, the plurality of halogen filter lamps are arranged at a central portion thereof, the plurality of halogen lamps are arranged outwardly of the plurality of halogen filter lamps, and the plurality of mercury lamps are arranged outwardly of the plurality of halogen lamps.

2. The solar simulator of claim 1, wherein the lamp bank is formed as a horizontal shape without a zenithal angle.

3. The solar simulator of claim 1, wherein the electrical panel further comprises a mercury lamp stabilizer for maintaining a constant voltage of the mercury lamps.

4. The solar simulator of claim 1, wherein the electrical panel includes a controller for controlling an operation of the temperature control unit in accordance with an internal signal and for controlling ON/OFF operation of the lamps constituting the lamp bank in accordance with a time signal, wherein the controller stores a temperature change reference value and an irradiance change reference value.

5. The solar simulator of claim 4, wherein a level of the time signal is divided such that the lamps are selectively turned on in accordance therewith, corresponding to the irradiance change reference value.

6. The solar simulator of claim 5, wherein in accordance with a time signal of each level, at least one halogen filter lamp, one halogen lamp and one mercury lamp are turned on.

7. The solar simulator of claim 5, wherein if the amount of irradiance is set to increase as the level of the time signal increases, the lamps turned on in accordance with a time signal of an upper level include those lamps turned on in accordance with a time signal of a lower level.

8. The solar simulator of claim 6, wherein if the amount of irradiance is set to increase as the level of the time signal increases, the lamps turned on in accordance with a time signal of an upper level include those lamps turned on in accordance with a time signal of a lower level.

9. The solar simulator of claim 4, wherein the internal signal controls the air conditioner and the cooling unit such that a temperature within the environment recreation laboratory corresponds to the temperature change reference value.

10. The solar simulator of claim 1, further comprising a perforated plate disposed on the same plane as the lamp bank but at a region where the lamp bank is not disposed, wherein the size of each perforation of the perforated plate is smaller than an interval between the lamps within the lamp bank.

11. A solar simulator using a combination of mercury lamps and halogen lamps, comprising:

a lamp bank including a plurality of halogen lamps, a plurality of mercury lamps and a plurality of halogen filter lamps being halogen lamps provided with infrared filters, respectively, wherein the plurality of halogen filter lamps are arranged at a center portion of the lamp bank, the plurality of halogen lamps are arranged outwardly of the halogen filter lamps, and the plurality of mercury lamps are arranged outwardly of the halogen filter lamps.

12. The solar simulator of claim 11, wherein the plurality of lamps constituting the lamp bank are arranged parallel to each other.

13. The solar simulator of claim 11, wherein the lamps constituting the lamp bank are selectively turned on for emitting illumination, corresponding to an actual daily change of the amount of irradiance.

14. The solar simulator of claim 11, wherein a level of lamp lighting is divided according to an actual daily change of the amount of irradiance, and at least one halogen filter lamp, one halogen lamp and one mercury lamp are turned on at each level of lamp lighting.

15. The solar simulator of claim 11, wherein when the level of the lamp lighting is divided according to an actual daily change of the amount of irradiance, lamps turned on at a lower level in which the amount of irradiance is lower are also turned on at an upper level in which the amount of irradiance is greater.

* * * * *